United States Patent [19]

Ehrenkranz

[11] Patent Number: 5,069,878
[45] Date of Patent: Dec. 3, 1991

[54] INTEGRITY PRESERVING AND DETERMINING URINE SAMPLE COLLECTION APPARATUS

[76] Inventor: Joel R. L. Ehrenkranz, Pleasantville Rd., New Vernon, N.J. 07976

[21] Appl. No.: 670,492

[22] Filed: Mar. 15, 1991

Related U.S. Application Data

[63] Continuation of Ser. No. 195,660, May 19, 1988, abandoned, which is a continuation-in-part of Ser. No. 29,727, Mar. 24, 1987, Pat. No. 4,769,215.

[51] Int. Cl.$^5$ .................. B01L 3/00; G01K 13/00; G01N 1/10; G01N 21/77
[52] U.S. Cl. ........................ 422/61; 422/58; 422/102; 128/760; 128/761; 128/771; 73/863.52
[58] Field of Search ............ 422/58, 61, 102; 128/760, 761, 771; 73/863.52; 4/144.1

[56] References Cited

U.S. PATENT DOCUMENTS

| | | | |
|---|---|---|---|
| 3,711,871 | 1/1973 | Sherin | 128/760 |
| 3,774,455 | 11/1973 | Seidler et al. | 422/58 |
| 4,064,760 | 12/1977 | Benjamin | 128/760 |
| 4,109,530 | 8/1978 | Kim | 73/863.52 |
| 4,211,749 | 7/1980 | Kantner | 422/102 |
| 4,408,905 | 10/1983 | Ehrenkranz | 4/144.1 |
| 4,473,530 | 9/1984 | Villa-real | 422/58 |
| 4,492,258 | 1/1985 | Lichtenstein et al. | 422/102 |
| 4,494,581 | 1/1985 | Gordon | 422/102 |
| 4,564,299 | 1/1986 | Ehrenkranz | 73/863.52 |
| 4,591,062 | 5/1986 | Sandhaus | 422/58 |

FOREIGN PATENT DOCUMENTS 2401892 7/1975 Fed. Rep. of Germany.

Primary Examiner—David L. Lacey
Assistant Examiner—Kimberly A. Trautman
Attorney, Agent, or Firm—Mathews, Woodbridge & Collins

[57] ABSTRACT

A drug testing urine sample collector includes a multiple tamper-proof system to make sure that freshly voided samples of urine are not replaced or adulterated. A chemical type thermometer is located in the reservoir to make sure that the urine sample is fresh when collected. A specific gravity sensitive ball valve restricts entry of a diluted urine sample into the reservoir. The cap for the reservoir also acts as a base for the collector and includes sample adulteration detection reagents. The collector structure prevents the sample from being emptied from the reservoir.

17 Claims, 6 Drawing Sheets

INTEGRITY PRESERVING AND DETERMINING URINE SAMPLE COLLECTION APPARATUS

CROSS REFERENCE TO RELATED APPLICATIONS

This application is a continuation of application Ser. No. 07/195,660, filed May 19, 1988, now abandoned, which is a continuation-in-part application based upon U.S. patent application Ser. No. 07/029,727 filed Mar. 24, 1987 and entitled "Integrity Preserving and Determining Urine Sample Collection Apparatus" by Joel R. L. Ehrenkranz now U.S. Pat. No. 4,769,215 issued on Sept. 6, 1988, the entire disclosure of which is hereby incorporated by reference.

BACKGROUND OF THE INVENTION

1. Field of the Invention

The invention relates to an apparatus for determining if a urine specimen is fresh and unadulterated and for preventing tampering with the urine specimen after it has been collected.

2. Description of Related Art

Drug use is generally recognized as a significant contributory factor in the current rise of accidents. Employers, government organizations, and others are increasingly using drug-screening and freedom from drugs as conditions of employment. There are three major problems. First, the collection and testing of urine samples must be simple and cost-effective. Second it has been felt necessary to monitor the taking of urine samples to guarantee the integrity of the test results. Third, the testing aspect, especially coupled with monitoring, has raised concerns about possible invasion of privacy. Accordingly, a need is recognized for a urine sample collector that is simple, straightforward, minimizes the invasion of an individual's privacy, and maximizes the integrity of the sample of urine taken. On Monday, Apr. 11, 1988, the Federal Government issued its final guidelines on Federal Workplace Drug Testing Programs in Volume 53, No. 69 of the Federal Register, pages 11970-11989.

The prior art discloses a few urine measuring devices incorporating a temperature sensor therein. Perhaps most relevant of that group is U.S. Pat. No. 4,564,299 entitled Body Liquid Temperature Measuring Device issued to Joel R. L. Ehrenkranz who is also the inventor of the device described in this disclosure. A chemical melting point thermometer is located in the bottom of the urine collecting receptacle. The primary purpose of the invention is to determine when a human female is close to ovulation.

The patent literature also describes devices, in very different contexts, which employ spill prevention devices in urine collecting embodiments. The purpose of those devices is to prevent spillage after the urine is collected and prior to its being destroyed. For example, U.S. Pat. Nos. 3,568,218 and 4,457,314 disclose anti-spill devices in two different types of urine collectors. The device in U.S. Pat. No. 4,457,314 is described as an "anti-back flow mechanism" and is employed only to prevent spillage of the contents. Other U.S. Pat. Nos. that disclose mechanisms for the purpose of preventing spillage include: 3,928,875; 4,059,124; 3,586,041 and 3,734,154.

Another class of urine collectors involve those designed to collect mid-stream urine samples. For example, U.S. Pat. No. 4,494,581 discloses a mid-stream urine collection device which describes, in FIG. 7 thereof, a mechanism in which a floating cork closes a flap after an initial sample of urine has been obtained so that the remaining specimen to be collected will be from the mid-stream. Other possibly relevant mid-stream urine collection devices include those described in the following U.S. Pat. Nos.: 4,064,760; 4,221,295 and 4,569,090.

Lastly, the following U.S. Pat. Nos. are cited as being of only general possible relevance: 4,396,113; 4,211,749; 4,443,896 and 4,466,445.

Insofar as understood, none of the prior art addresses the problems inherent in a drug testing program where the drug sample collecting device has to be virtually tamper-proof, easy to use, and maintain the individual's right of privacy.

SUMMARY OF THE INVENTION

Briefly described, the invention comprises a urine collection device specifically appropriate for use in drug screening programs. A urine receiving reservoir includes a temperature measuring device, such as a chemical type thermometer, located in a chamber for documenting the freshness of the urine sample immediately after voiding. Urine enters the reservoir through a channel near the center of the device. In the preferred embodiment, the channel includes a specific gravity sensitive mechanism which only passes urine specimens into the collector if the urine specimen is within the correct range of acceptable specific gravity levels. In other words, if a sample of urine is adulterated with water, the reservoir will not accept the urine sample. Also the device is constructed in such a way that as urine fills the reservoir air escapes through vent holes into the collection bowl. The air holes are of sufficiently small diameter and the center channel is of sufficient depth such that when the urine collector is inverted substantially all of the urine sample remains in the collector. Thus the urine sample can be removed from the collector in only a tamper-evident way.

The inside of the reservoir cap which resides in the base of the collector until the sample is taken includes chemical reagent stations to further discourage or detect tampering or adulteration. One reagent station can determine if the urine sample has been watered down by detecting the specific gravity of the sample. A second reagent station measures the pH of the urine. A third station includes a chemical reagent that helps determine if an enzyme poison, like bleach, dye, detergent or antibody has been added to the urine sample in order to disguise the presence of drugs such as cannabis, cocaine, opiates, amphetamines, sedatives and hallucinogenics.

Because the urine collector is virtually tamper-proof, it eliminates or greatly reduces the need to have the voiding procedure humanly monitored by another individual. This in turn increases the individual's privacy while also guaranteeing that the employer has a fresh, unadulterated, high integrity urine sample.

These and other features of the invention will be more fully understood by reference with the following drawings.

DETAILED DESCRIPTION OF THE INVENTION

During the course of this description like numbers will be used to identify like elements according to the different figures which illustrate the invention.

Figure 1:
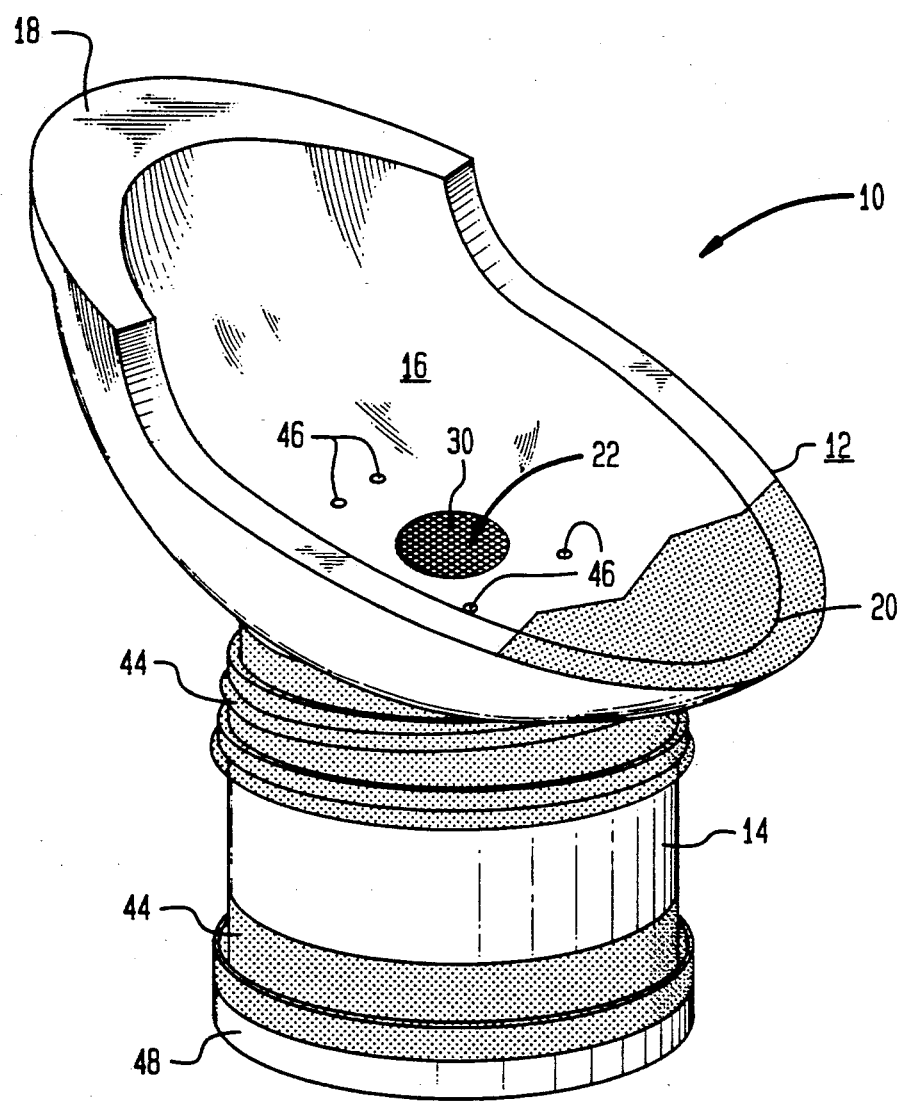
FIG. 1 is a perspective view of the preferred embodiment of the invention.
Figure 2:
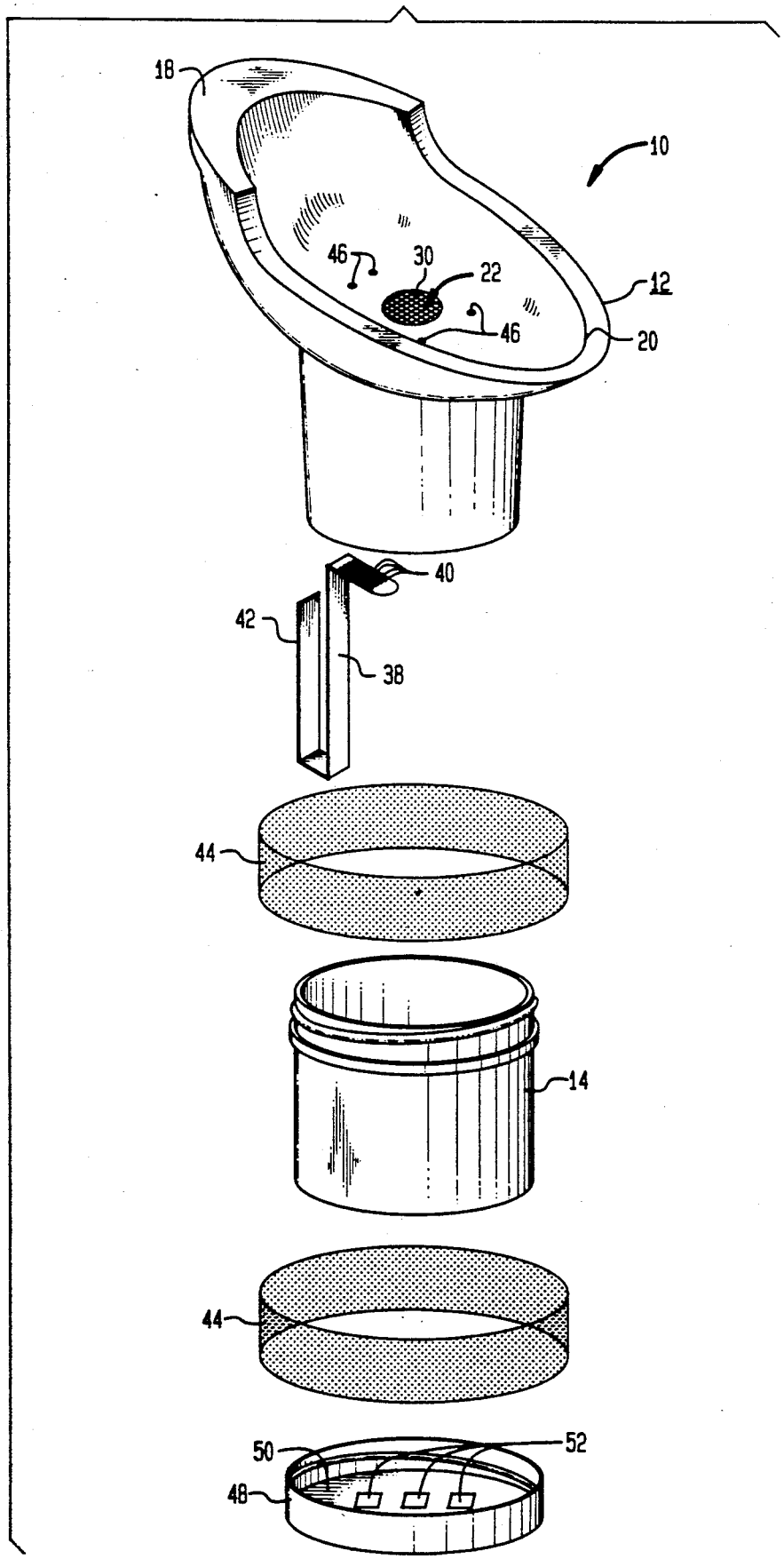
FIG. 2 shows an exploded view of the receptacle.
Figure 3A:
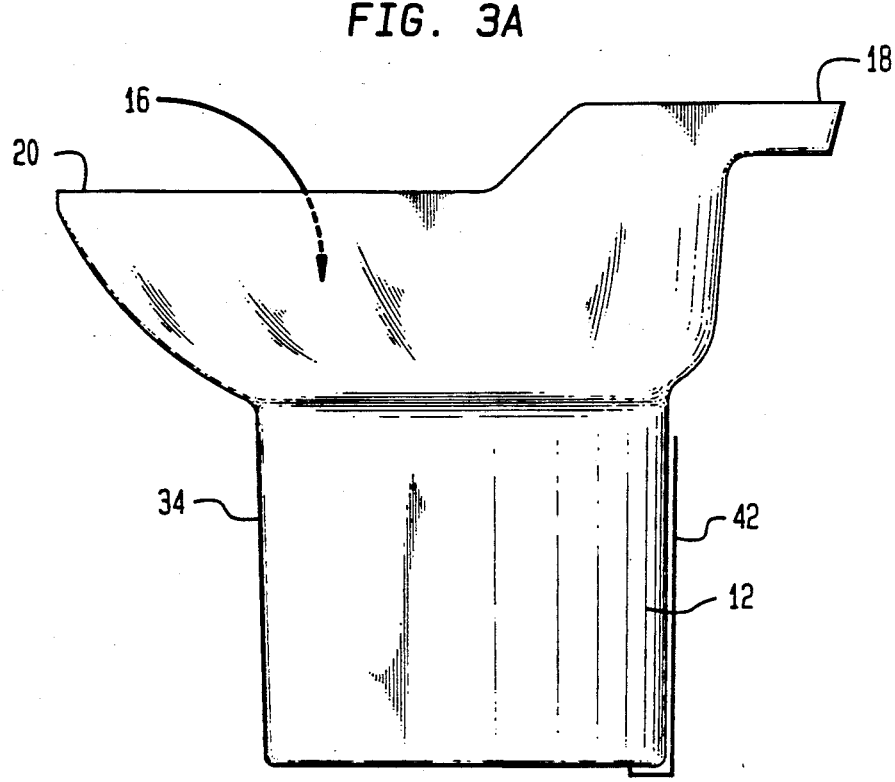
FIG. 3A is a side elevation of the collector.
Figure 3B:
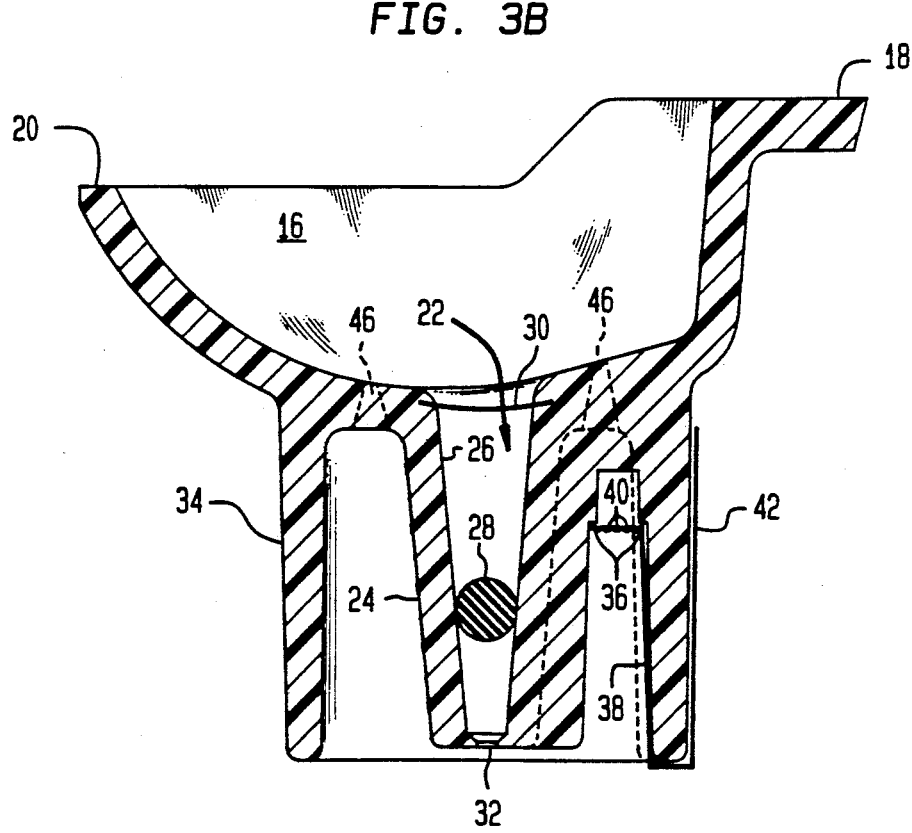
FIG. 3B is a cross-sectional view taken along lines B—B of FIG. 3D.
Figure 3C:
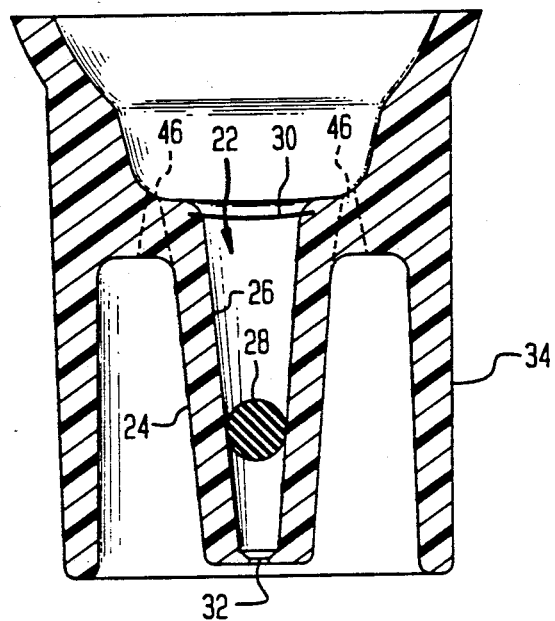
FIG. 3C is another cross-sectional view taken along lines C—C of FIG. 3D.
Figure 3D:
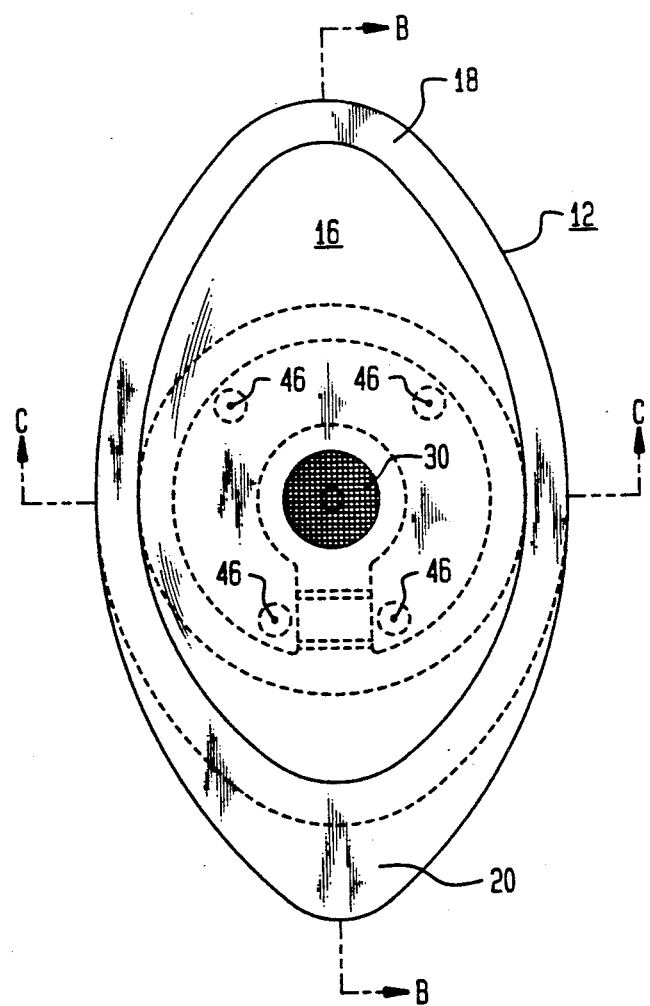
FIG. 3D is a top plan view of the collector.
Figure 3E:
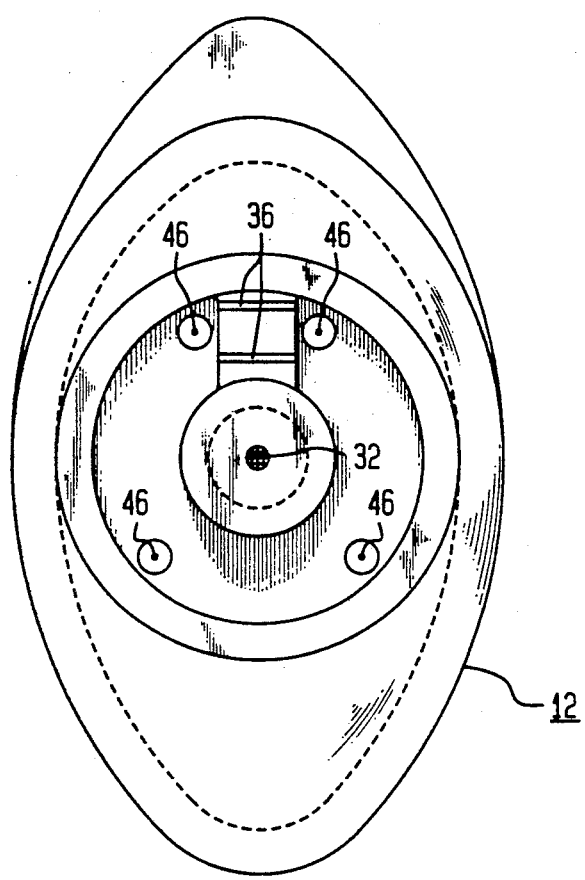
FIG. 3E is a bottom plan view of the collector.

FIGS. 1 and 2 illustrate the preferred embodiment of the collector 10, which includes a generally elliptical collection apparatus 12 and cylindrical reservoir jar 14. The collection apparatus 12 includes a collection bowl 16 having both a raised portion 18 which acts as both a pouring spout and an anti-splatter shield and a lower rear rim 20. Reservoir jar 14 is intended to hold a urine sample in the range of 60 to 120 cc, with a preferred total capacity of approximately four (4) ounces.

The accuracy of the invention 10 depends upon minimizing temperature variations due to surface cooling, or heat conducted from the base of the container. Accordingly the base portion of the collection apparatus 12 which is the reservoir jar 14 is of restricted surface area as compared to the upper collection bowl portion 12. Cap 48 at the bottom of the reservoir jar 14 is provided in part to provide additional insulation from ambient temperatures. After use, the cap 48 can be affixed to the top of reservoir jar 14 for storage if the sample is to be retained. Collector 12 also includes a urine input aperture 22 which permits urine to travel from collection bowl 16 into reservoir jar 14.

FIGS. 3A through 3E illustrate the preferred embodiment of collector 12. In operation urine enters collection bowl 16 from the donor and exits bowl 16 through aperture 22 into tapered channel 26 of urine input tube 24. Tapered channel 26 is tapered in such a way as to support ball 28 at approximately the midpoint between urine input aperture 22 and urine exit aperture 32. The tapered channel 26 preferably has an entrance diameter of approximately one-half (½) inch and an exit diameter of approximately three-eighths (⅜) inch. Ball 28 in combination with urine input tube 24, tapered channel 26, and the cage 30 on top of channel 26 which keeps ball 28 in the channel is important to the operation of invention 10. Ball 28 has a specific gravity between 1.001 and 1.002. Thus ball 28 acts like a specific gravity sensitive valve which only permits a urine sample to flow into reservoir jar 14 if the urine sample is within a desired range of specific gravity. Ball 28 is kept in channel 26 by cage 30 at the top and the restrictive taper of channel 26 toward aperture 32 at the bottom. The purpose of this first stage of invention 10 is only to collect specimens of urine that fall above a predetermined range of specific gravity. It is useful to collect urine in this fashion in order to prevent subjects from watering their urine down thereby diluting the accuracy of the test results. Normal urine has a specific gravity of 1.003–1.040. Accordingly, the ball 28 with a specific gravity of 1.001–1.002 only floats in urine having a specific gravity of 1.002 or greater. Accordingly, adulterated urine samples with a specific gravity less than 1.001 do not get collected in reservoir jar 14.

If urine 60 successfully flows through the ball valve 28, then it collects in reservoir jar 14. Collector 12 has a cylindrical wall base 34 extending below collection bowl 16. Inside the wall 34 at the upper inside exists pedestal 36 for supporting chemical thermometer 38. While a pedestal is illustrated in the preferred embodiment, it will be understood that the thermometer 38 may also be adhesively affixed to the side wall 34 or affixed by either means. This is the second stage of urine testing. It has been found that there is reliable discrimination on the basis of temperature between fresh and previously collected urine samples. Other experiments where the urine sample has been adulterated by the addition of chemicals takes the temperature outside the range of a normal freshly voided urine sample. The temperature range for a normal freshly voided urine sample is 96.4° F. to 100.4° F.

Thus chemical reagent thermometer 38 takes and stores the temperature of the urine sample until it can be read. (It stores this information in a chemical dot array 40 at the end of thermometer 38). Thermometer 38 can be removed from the collection apparatus 12 by pulling on handle 42 or, if attached to the inside of the jar, can remain in specimen.

Figure 5:
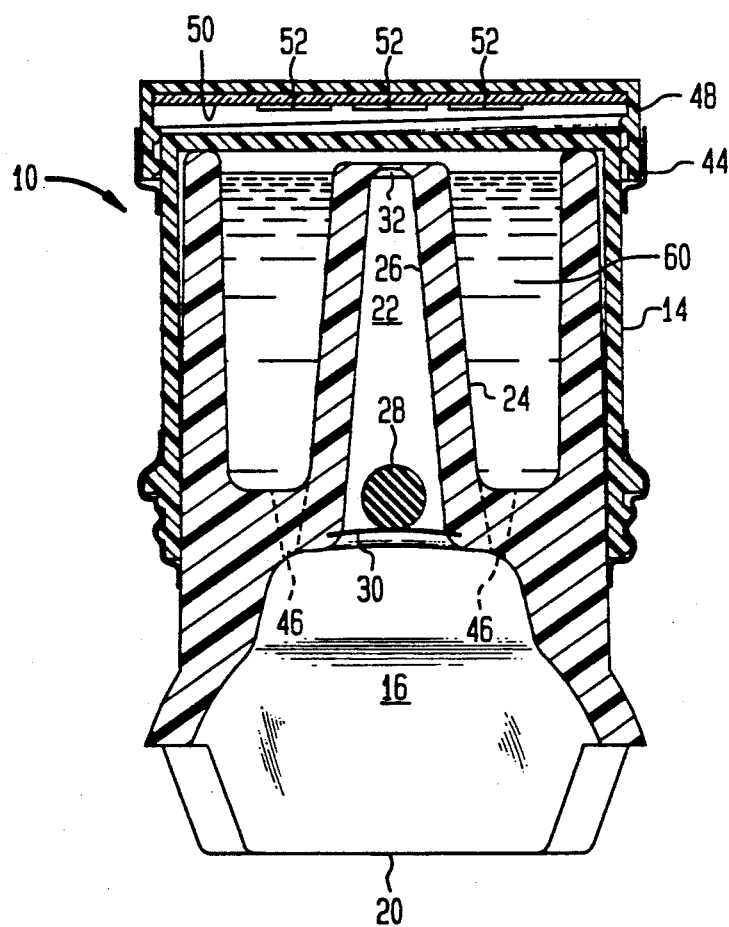
FIG. 5 illustrates the collector inverted showing the manner in which the urine sample is retained.

Collector 12 is attached to reservoir jar 18 through the use of tamper-evident tape 44 which attaches to the upper outside surface of reservoir jar 14 and the lower outside surface of collection bowl 16. Tamper-evident tape 44 both seals the collector 12 to the reservoir jar 18 and provides a detectable means of determining if the collector 12 has been partially or completely separated from reservoir jar 14. Because the tape 44 will provide a substantially air-tight seal it is necessary to have a means to permit air to escape, i.e. vent, from reservoir jar 14 as it fills with urine. Air vent holes 46 through collection bowl 16 provide air escape means from the reservoir jar 14. These air holes 46 are of sufficient diameter and number that they will permit air to escape but because of the surface tension of the urine will not permit the urine to escape if the collector is inverted as shown in FIG. 5. Air vent holes 46 should be as small as possible, i.e smaller than 1/32" and preferably 1/64".

Reservoir jar 14 is a standard urine sample collection jar such as those available from Lerman Container Corporation, 10 Great Hill Road, Naugatuck, Conn. 06770. Prior to analysis of the sample, cap 48 is removably attached to the bottom of reservoir jar 14. Cap 48 and liner 50 are also available from the Lerman Container Corporation. The cap 48 could be attached by either friction fit to the bottom of reservoir jar or by tamper-evident tape 44.

Figure 4A:
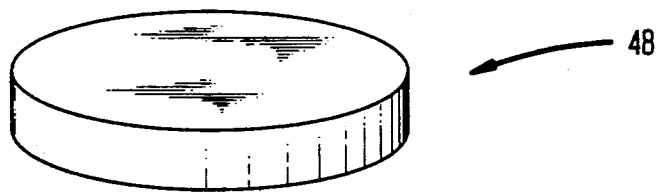
FIG. 4A illustrates the cap top.
Figure 4B:
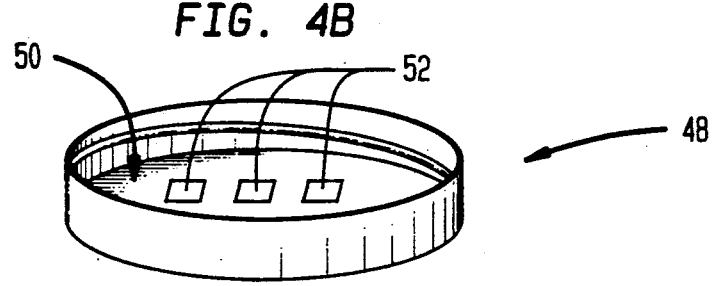
FIG. 4B illustrates the cap bottom.

FIGS. 4A and 4B show the cap 48. Cap 48 represents the third stage of testing. Cap 48 includes an insulation liner 50 inside the cap for the purpose of insulating the urine sample from the ambient temperature when the cap 48 is on the base of the reservoir jar 14. Cap 48 also contains reagents 52 which do additional testing of the urine sample. As has been disclosed in my co-pending application Ser. No. 07/029,727 filed on Mar. 24, 1987, these reagents can test for specific gravity, pH, poison, and other features or adulterants of the urine. The pH normal range of unadulterated urine is 4–8. These solid phase reagents 52 react with the urine sample after the collector 12 has been separated from reservoir jar 14 and cap 48 has been removably attached to the top of the reservoir jar 14. It would, of course, be necessary to destroy the integrity of the tamper-evident tape to accomplish this third stage of testing. The tamper evident tape 44 is preferably applied by shrink wrapping, but may be applied in other ways. The fourth stage of testing, incidentally, would be testing the urine sample for specific drug content.

In summary, the present invention is capable of preventing urine donors from tampering with a sample of urine either by means by substitution, adulteration, or dilution. The sample 60 is protected from substitution because the reservoir cannot be emptied if inverted, as shown in FIG. 5, and because the temperature thermometer insures that only freshly voided samples of urine are received in the reservoir. Protection against sample adulteration is insured in part by the pH strip on the bottom of the cap and because many urine adulterants produce exothermic reactions which would cause the thermometer inside the reservoir to indicate that the sample had exceeded an acceptable temperature threshold. Lastly, protection against sample dilution is provided, in large part, by the specific gravity sensitive ball valve which only permits non-diluted urine samples having a specific gravity exceeding 1.002 to enter into the reservoir. Additional protection is provided by the use of tamper evident tapes to insure that the reservoir and the collection apparatus are not separated by anyone other than authorized personnel.

While the invention has been described with reference to the preferred embodiment thereof, it will be appreciated by those of ordinary skill in the art that various modifications can be made to the structure and function of the invention without departing from the spirit and the scope of the invention as a whole.

I claim:

1. A drug testing urine sample collection kit apparatus comprising:
   a reservoir having a cavity therein for holding a sample of urine;
   a collection means for collecting urine and transmitting it to said reservoir, said collection means including a bowl connectable to said reservoir, a tube connected to the bottom of said bowl and including a channel therein for communicating from said bowl into the cavity of said reservoir, said channel including a taper from a larger entrance aperture in the area of the bottom of said bowl to a smaller exit aperture near the discharge end of said tube;
   a sphere having a specific gravity in the range of 1.001 to 1.002 and located in said tapered channel wherein said sphere prevents liquid with a specific gravity of less than about 1.002 from passing into said reservoir;
   a keeper means for preventing said sphere from escaping from the large entrance aperture of said channel;
   air venting means in said bowl for permitting air to escape from said reservoir as it fills up with urine and for preventing any substantial amount of urine from escaping from said reservoir when said apparatus is inverted; and,
   a temperature detecting means for measuring the temperature of the urine as it is being collected in said reservoir and for providing an indication of the collection temperature for a prolonged period of time after collection, thereby serving as an indication that the sample was fresh and unadulterated when collected,
   wherein said tube prevents said urine from being emptied from said reservoir when said apparatus is inverted.

2. The apparatus of claim 1 further comprising:
   tamper-evident tape attachable to said reservoir and said collection means.

3. The apparatus of claim 2 further comprising:
   a cap locatable on the bottom of said reservoir including threads thereon for threadably engaging threads on an upper edge of said reservoir when said reservoir is removed from said collection means.

4. The apparatus of claim 3 further comprising:
   insulation means located on the inside on said cap for preventing heat transfer to and from the base of said reservoir.

5. The apparatus of claim 4 further comprising:
   sample adulteration detection means located on the inside of said cap for detecting if said sample has been adulterated.

6. The apparatus of claim 5 wherein said channel is tapered from said larger entrance aperture approximately ½" in diameter to said smaller exit aperture approximately ⅜" in diameter.

7. The apparatus of claim 6 wherein said air venting means comprises holes approximately 1/64" in diameter.

8. The apparatus of claim 7 further comprising:
   a downwardly extending sidewall skirt attached to said bowl for being positioned into said reservoir beyond said temperature detecting means.

9. A collection kit apparatus for use with a drug testing urine sample collector including a reservoir having a cavity therein for holding a sample of urine, said collection apparatus comprising:
   a bowl connectable to said reservoir;
   an open-ended tube connected to the bottom of said bowl and including a channel for communication from said bowl into the cavity of said reservoir;
   a temperature detecting means for measuring the temperature of the urine as it is being collected in said reservoir and for providing an indication of the collection temperature for a prolonged period of time after collection, thereby serving as an indication that the sample was fresh and unadulterated when collected; and,
   air venting means in said apparatus for permitting air to escape from said reservoir as it fills up with urine and for preventing any substantial amount of urine from escaping from said reservoir when said apparatus is inverted,
   wherein said tube prevents said urine from being emptied from said reservoir when said apparatus is inverted.

10. The apparatus of claim 9 further comprising:
    a downwardly extending sidewall skirt attached to said bowl for being positioned into said reservoir beyond said temperature detecting means.

11. The apparatus of claim 10 further comprising:
    tamper-evident tape means attachable to said reservoir and to said apparatus for providing an indication that the connection between said reservoir and said apparatus had been tampered with.

12. The apparatus of claim 11 wherein said channel in said tube is tapered from a large entrance aperture near said bowl to a smaller exit aperture near the discharge end of said tube.

13. The apparatus of claim 12 further comprising:

a sphere having a specific gravity in the range of 1.001 to 1.002 and located in said tapered channel; and, a keeper means for preventing said sphere from escaping from the large entrance aperture of said channel, wherein said sphere prevents liquid with a specific gravity less than 1.001 from passing into said reservoir.

14. The apparatus of claim 13 wherein said channel is tapered from said larger entrance aperture having a diameter of approximately ¼" to said smaller exit aperture having a diameter of approximately ⅜".

15. The apparatus of claim 14 wherein said air venting means comprises holes having a diameter of approximately 1/64" where they enter said bowl.

16. A collection kit apparatus for use with a drug testing urine sample collector including a reservoir having a cavity therein for holding a sample of urine, said collection apparatus comprising:

a bowl connectable to said reservoir;

an open-ended tube connected to the bottom of said bowl and including a channel for communication from said bowl into the cavity of said reservoir;

specific gravity means located within said channel for preventing urine with a specific gravity less than 1.002 from passing into said reservoir;

air escape means in said apparatus for permitting air to escape from said reservoir as it fills up with urine and for preventing any significant amount of urine from escape from said reservoir when said apparatus is inverted; and, temperature detecting means for measuring the temperature of the urine as it is being collected in said reservoir and for providing an indication of the collection temperature for a prolonged period of time after collection, thereby serving as an indication that the sample was fresh when collected.

17. A collection kit apparatus including a reservoir having a cavity therein for holding a sample of urine, said collection apparatus comprising:

a bowl connectable to said reservoir;

an open-ended tube connected to the bottom of said bowl and including a channel for communication from said bowl into the cavity of said reservoir;

air venting means in said apparatus for permitting air to escape from said reservoir as it fills up with urine and for preventing any substantial amount of urine from escaping from said reservoir when said apparatus is inverted, wherein said tube prevents said urine from being emptied from said reservoir when said apparatus is inverted.

* * * * *